United States Patent
Heng et al.

(10) Patent No.: US 9,534,997 B2
(45) Date of Patent: Jan. 3, 2017

(54) APPARATUS AND METHOD FOR VISIOMETRIC DISINTEGRATION

(71) Applicant: National University of Singapore, Singapore (SG)

(72) Inventors: Paul Wan Sia Heng, Singapore (SG); Parind Mahendrakumar Desai, Singapore (SG); Celine Valeria Liew, Singapore (SG)

(73) Assignee: National University of Singapore, Singapore (SG)

( * ) Notice: Subject to any disclaimer, the term of this patent is extended or adjusted under 35 U.S.C. 154(b) by 356 days.

(21) Appl. No.: 14/249,854

(22) Filed: Apr. 10, 2014

(65) Prior Publication Data
US 2014/0305225 A1 Oct. 16, 2014

Related U.S. Application Data (60) Provisional application No. 61/810,837, filed on Apr. 11, 2013.

(51) Int. Cl.
*G01N 13/00* (2006.01)
*G01N 33/15* (2006.01)

(52) U.S. Cl.
CPC .............. *G01N 13/00* (2013.01); *G01N 33/15* (2013.01); *G01N 2013/006* (2013.01)

(58) Field of Classification Search
CPC .. G01N 33/15; G01N 13/00; G01N 2013/006; G01N 21/9508
(Continued)

(56) References Cited

U.S. PATENT DOCUMENTS 3,791,222 A * 2/1974 Goodhart .............. B01F 1/0011
422/82.09
4,855,821 A * 8/1989 Swon ..................... G01N 13/00
348/89
(Continued)

FOREIGN PATENT DOCUMENTS

| JP | 2001141718 | 5/2001 |
| JP | 2004233332 | 8/2004 |

(Continued)

OTHER PUBLICATIONS

Bi, Y., Sunada, H., Yonezawa, Y., Danjo, K., Otsuka, A., Iida, K., 1996. Preparation and evaluation of a compressed tablet rapidly disintegrating in the oral cavity. Chem. Pharm. Bull. 44(11), 2121-2127.

(Continued)

*Primary Examiner* — Hezron Williams
*Assistant Examiner* — Marrit Eyassu
(74) *Attorney, Agent, or Firm* — Hamilton, Brook, Smith & Reynolds, P.C.

(57) ABSTRACT

In one version of the invention, an apparatus intended for determining the disintegration time of rapidly disintegrating tablets is designed with a disintegration cell having two liquid inlets and outflow from the top. Visualization of tablet inside the disintegration cell is conducted using a camera aided by a base light source and images captured using a computer or any other recording system. Disintegration medium is introduced into the disintegration cell through both inlets to produce a swirling motion and images of the tablet disintegration process are captured. The captured images are analyzed in real-time or off-line, to determine the tablet disintegration time. A visual non-recording method using projected image may also be used.

21 Claims, 8 Drawing Sheets

(58) Field of Classification Search
USPC .............................. 73/866, 865.8; 435/288.7
See application file for complete search history.

(56) References Cited

U.S. PATENT DOCUMENTS

| | | | | |
|---|---|---|---|---|
| 5,816,701 | A * | 10/1998 | Martin | B01F 1/0011 366/140 |
| 2005/0003550 | A1* | 1/2005 | Kyne | G01N 33/15 436/2 |
| 2006/0288805 | A1* | 12/2006 | Das | G01N 33/15 73/866 |
| 2007/0160497 | A1* | 7/2007 | Hughes | G01N 13/00 422/68.1 |

FOREIGN PATENT DOCUMENTS

| | | |
|---|---|---|
| JP | 2008032482 | 2/2008 |
| JP | 2008064620 | 3/2008 |
| JP | 2008082877 | 4/2008 |
| JP | 2010164415 | 7/2010 |

OTHER PUBLICATIONS

Desai, P.M., Liew, C.V., Heng, P.W.S., 2013. Assessment of disintegration of rapidly disintegrating tablets by a visiometric liquid jet-mediated disintegration apparatus. Int. J. Pharmaceut. 442(1-2), 65-73.

Morita, Y., Tsushima, Y., Yasui, M., Termoz, R., Ajioka, J., Takayama, K., 2002. Evaluation of the disintegration time of rapidly disintegrating tablets via a novel method utilizing a CCD camera. Chem. Pharm. Bull. 50(9), 1181-1186.

\* cited by examiner

APPARATUS AND METHOD FOR VISIOMETRIC DISINTEGRATION

RELATED APPLICATION

This application claims the benefit of U.S. Provisional Application No. 61/810,837, filed on Apr. 11, 2013. The entire teachings of the above application are incorporated herein by reference.

BACKGROUND OF THE INVENTION

One of the most important characteristics of a tablet formulation is its disintegration phenomenon. The disintegration time of a conventional tablet is commonly determined using United States Pharmacopoeia (USP) disintegration apparatus. However, no specific pharmacopoeial apparatus has been identified to determine the disintegration time of rapidly disintegrating tablets (RDTs). It is often difficult to precisely determine the disintegration time of RDTs using USP disintegration apparatus when the tablet disintegration process is very rapid. Moreover, USP disintegration apparatus has limitations in discriminating between disintegration times of different RDTs. Thus, it is necessary to develop a disintegration apparatus capable of determining precisely the disintegration time of RDTs.

SUMMARY OF THE INVENTION

In accordance with a version of the invention, there is provided a disintegration test method and apparatus that can evaluate the disintegration process of rapidly disintegrating tablets (RDTs) or fast disintegrating dosage forms in a simple, accurate and reproducible manner.

A version of the invention is related to the concept and design of a disintegration apparatus that is particularly useful to determine accurately the disintegration time of rapidly disintegrating tablets (RDTs) upon wetting.

In one version of the invention, an apparatus intended for determining the disintegration time of rapidly disintegrating tablets is designed with a disintegration cell having two liquid inlets and outflow from the top. Visualization of tablet inside the disintegration cell is conducted using a camera aided by a base light source and images captured using a computer or any other recording system. Disintegration medium is introduced into the disintegration cell through both inlets to produce a swirling motion and images of the tablet disintegration process are captured. The captured images are analyzed in real-time or off-line, to determine the tablet disintegration time. A visual non-recording method using a projected image may also be used.

It is an object of a version of the present invention to provide a disintegration apparatus for accurate determination of the disintegration time of RDTs or fast disintegrating tablets.

Another object of a version of the present invention is to provide a disintegration apparatus with the facility to image the disintegration process and enable real-time documentation of the measurement.

In one version of the invention, there is provided an apparatus for determining the disintegration time of a disintegrating dosage form. The apparatus comprises a disintegration cell configured to contain the dosage form, and a plurality of liquid jet inlets configured to introduce a disintegration medium into the disintegration cell to produce a swirling shear force of the disintegration medium within the disintegration cell. The disintegration cell comprises an overhead outlet configured to remove, from the disintegration cell, overflowing disintegration medium and a plurality of disintegrated fragments of the dosage form.

In further, related versions, the disintegration cell may be configured to permit visualization of the dosage form through at least a portion of the disintegration cell. The disintegration cell may comprise a transparent surface configured to allow passage of light from a light source to permit visualization of the dosage form; or may comprise a reflecting surface configured to reflect light, received from a light source, to permit visualization of the dosage form. The apparatus may further comprise a camera mounted to permit the visualization of the dosage form; and may further comprise a collimating lens mounted to pass light, received from the disintegration cell, to the camera. A data acquisition system may be configured to receive from the camera an electronic signal indicative of an image of at least a portion of the disintegration cell. The apparatus may further comprise a liquid pump in fluid communication with the disintegration cell. An image projection system may be mounted to permit visualization of the dosage form. The disintegration cell may be cylindrical. The dosage form may comprise a tablet.

In other, related versions, the apparatus may further comprise a retaining mesh configured to permit passage of the overflowing disintegration medium and the plurality of disintegrated fragments of the dosage form to be removed from the disintegration cell, and to retain fragments of the dosage form that are larger than a mesh aperture size of the retaining mesh. Each of the plurality of liquid jet inlets may comprise a lower inlet base at a same level as a base of the disintegration cell. At least one of the plurality of liquid jet inlets may comprise an inlet from the group consisting of: an L-shaped inlet; an inlet comprising a C-shape; and a triangle-shaped inlet. The plurality of liquid jet inlets may be configured to produce the swirling shear force at a substantially consistent level of shear force that disintegrates the dosage form in a time substantially equivalent to a disintegration time produced by gentle mastication of the dosage form, and to enable breakdown of the dosage form.

In another version of the invention, there is provided a method for determining the disintegration time of a disintegrating dosage form. The method comprises introducing a disintegration medium into a disintegration cell through a plurality of liquid jet inlets, the disintegration cell containing the dosage form, the introducing producing a swirling shear force of the disintegration medium within the disintegration cell. Overflowing disintegration medium and a plurality of disintegrated fragments of the dosage form are removed from the disintegration cell through an overhead outlet. A disintegration process of the dosage form is imaged through at least a portion of the disintegration cell to permit determining a disintegration end point time of the dosage form.

In further, related versions, a video camera or an image projection system may be used to image the disintegration process. The method may comprise using a data acquisition system to receive an electronic signal indicative of an image of at least a portion of the disintegration cell, and performing image analysis of the electronic signal to determine the disintegration end point time of the dosage form.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Figure 1A:
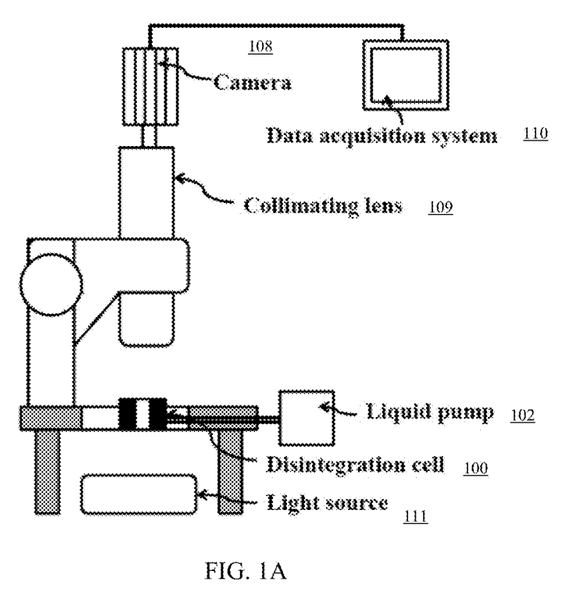
FIG. 1A is a schematic view of a disintegration apparatus using a video camera and data acquisition system, in accordance with a version of the invention.
Figure 1B:
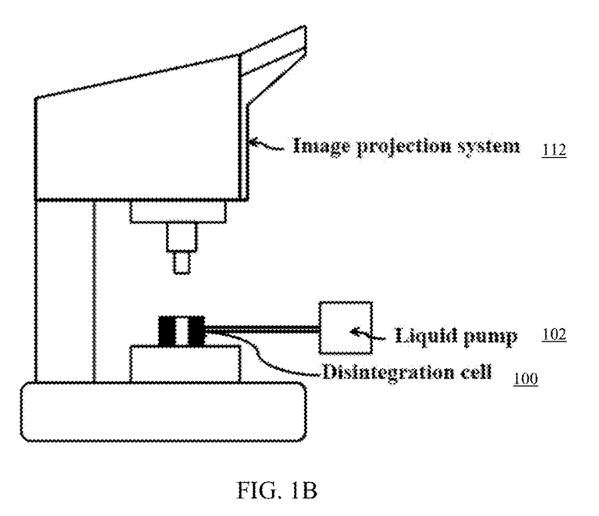
FIG. 1B is a schematic view of a disintegration apparatus using an image projection system, in accordance with a version of the invention.
Figure 2:
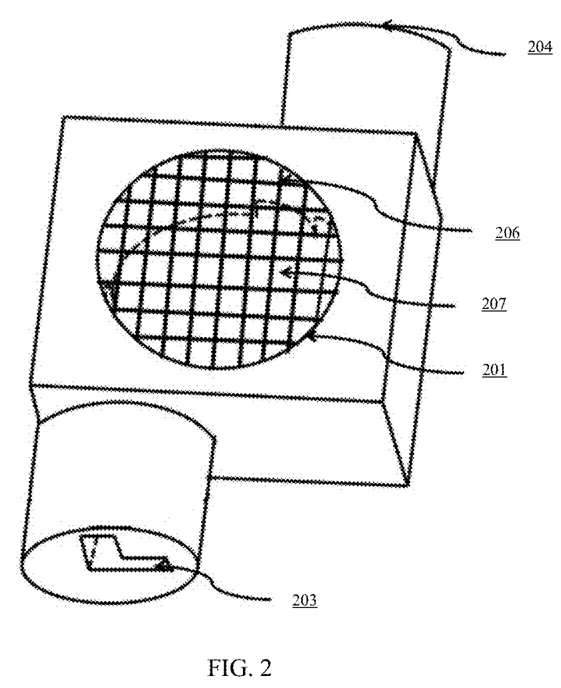
FIG. 2 is a perspective view of a disintegration cell in accordance with a version of the invention.
Figure 3:
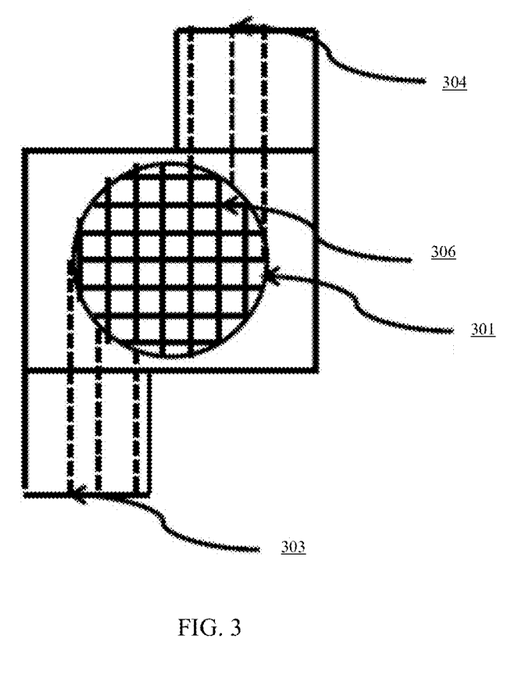
FIG. 3 is a top view of a disintegration cell in accordance with a version of the invention.
Figure 4:
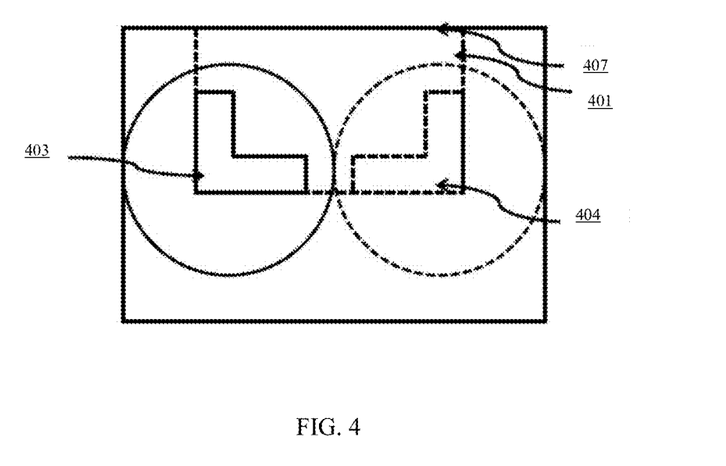
FIG. 4 is a side view of a disintegration cell in accordance with a version of the invention.

FIG. 1A is a schematic view of a disintegration apparatus using a video camera and data acquisition system; FIG. 1B is a schematic view of a disintegration apparatus using an image projection system; FIG. 2 is a perspective view of a disintegration cell; FIG. 3 is a top view of a disintegration cell; FIG. 4 is a side view of a disintegration cell; all in accordance with a version of the invention.

With reference to FIGS. 1A-4, in accordance with a version of the invention, the disintegration cell 100 (see FIGS. 1A and 1B) includes a cylindrical cell 201/301/401 (see FIGS. 2, 3 and 4, respectively), with dimensions of 16 mm or thereabouts diameter and 10 mm or thereabouts in depth to place the RDT. For example, the disintegration cell 100 may be between about 10 mm and about 20 mm in diameter, and between about 5 mm and about 15 mm in depth. A liquid pump 102 (see FIGS. 1A and 1B) is used to deliver the disintegration medium to the disintegration cell 100. The disintegration medium may, for example, be delivered at a flow rate of between about 65 mL/min and about 105 mL/min. Two L- (or C- or triangle) shaped disintegration medium inlets 203/204, 303/304 and 403/404 (see FIGS. 2, 3 and 4, respectively) are used to send the disintegration medium inside the cylindrical cell 201 where disintegration medium comes in contact with RDT and disintegration of the RDT is effected. Lower bases 505a/505b/505c (see FIGS. 5A-5C) of both inlets 203/204, 303/304 and 403/404 are at the same level as the base of the cylindrical cell 201/301/401.

Figure 5A:
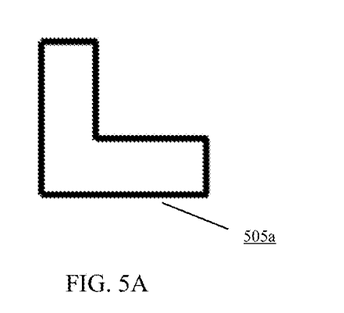
FIG. 5A is a side view of an L-shaped disintegration medium inlet shape, in accordance with a version of the invention.
Figure 5B:
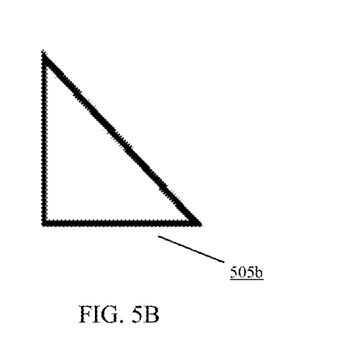
FIG. 5B is a side view of a triangle shaped disintegration medium inlet shape, in accordance with a version of the invention.
Figure 5C:
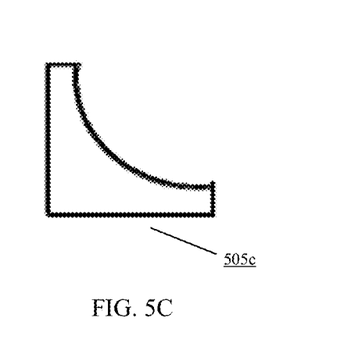
FIG. 5C is a side view of a disintegration medium inlet comprising a C-shape, in accordance with a version of the invention.

Particular shapes of inlets in accordance with a version of the invention are shown in FIGS. 5A-5C. FIG. 5A is a side view of an L-shaped disintegration medium inlet shape; FIG. 5B is a side view of a triangle shaped disintegration medium inlet shape; and FIG. 5C is a side view of a disintegration medium inlet comprising a C-shape; in accordance with versions of the invention. These shapes provide a swirling action of disintegration medium onto the disintegrating tablet as well as allow rapid and sufficient wetting at the lower surface of tablet, both of which permit completely removing the disintegrated tablet fragments from the disintegration cell. The disintegrated tablet fragments along with disintegration medium get removed from the disintegration cell and if needed, via a retaining mesh 206/306 (see FIGS. 2 and 3) of 2 mm or thereabouts aperture size, towards the outlet 207/407 (see FIGS. 2 and 4). For example, the mesh aperture size may be between about 1 mm and about 3 mm. The disintegration process can be visualized or captured by a video camera 108 mounted with collimating lens 109, and images can be transferred to a data acquisition system 110, such as a recording device or computer (see FIG. 1A). Light is applied from a light source 111 in a base to get a clearer view of the disintegration process. Glass, plastic, metal or a combination of materials can be used to construct the apparatus. The flat bottom surface of the apparatus can be made of a transparent material to allow the passing of light from the base light source 111 through the cell 100 for visualization of the tablet within. Alternatively, a reflecting system may be used with top lighting. For example, an image projection system 112 is shown in FIG. 1B.

The present invention may be used as a disintegration apparatus for normal tablets (i.e., tablets other than RDTs), and if so, the disintegration apparatus is preferably operated by re-circulating the disintegration medium.

In accordance with a version of the invention, the disintegration apparatus consists of a cylindrical disintegration cell 201/301/401 for holding the tablet and two or more liquid inlets 203/204, 303/304 and 403/404, and an overflow outlet 207/407 with or without a retention mesh 206/306 for the flow of disintegration medium introduced by pumping via liquid jet inlets 203/204, 303/304 and 403/404 into the disintegration cell 100. A video camera 108 is used to capture the disintegration process. The disintegration medium is pumped into the disintegration cell 100 through liquid jet inlets 203/204, 303/304 and 403/404, usually two, from opposite ends. Tablet disintegration or break up into fragments is effected when contact is made with disintegration medium. The disintegration process is captured in real-time using a video camera 108 or an image projection system 112. The disintegration medium along with disintegrated tablet fragments leaves the disintegration cell 100 with the overflowing liquid. Alternatively, a screening mesh 206/306 may be used to retain fragments larger than the mesh aperture size. The end point of the disintegration process is considered when no large fragments are present in the disintegration cell or occasional residues of disintegrated mass settling on the base, wall or mesh of the disintegration cell and become immobilized. The disintegration process can be documented by the real-time video images. An automated image analysis software system may also be used to determine the disintegration end point.

The liquid jet inlets 203/204, 303/304 and 403/404 can be configured to produce a swirling shear force at a substantially consistent level of shear force that disintegrates the dosage form in a time substantially equivalent to a disintegration time produced by gentle mastication of the dosage form, and to enable breakdown of the dosage form. As used herein, a "substantially consistent level of shear force" means a shear force that varies by less than 20% over the course of the distintegration of the dosage form. As used herein, "gentle mastication" means mastication using average forces that are employed by the average consumer of a dosage form when masticating the dosage form. As used herein, "breakdown" of the dosage form means that the dosage form has reached a condition in which a disintegration time of the dosage form has ended.

As used herein, a "dosage form" means a pharmaceutical product in the form in which it is marketed for use, such as a mixture of active drug components and nondrug components (e.g., excipients), along with other non-reusable material such as, for example, a capsule shell. The dosage form can include solid or semisolid dosage forms, such as pills, tablets capsules and thin films, and can include natural or herbal forms.

As used herein, a "swirling shear force" means a force produced by unaligned forces pushing one part of a liquid in one direction, and another, unaligned, part of the liquid in the opposite direction.

As used herein, a "disintegration time" or "disintegration end point time" means a duration of time required for a dosage form to disintegrate to a state in which no large fragments are present in a disintegration cell containing the dosage form, or in which only occasional residues of disintegrated mass settle on the base, wall or mesh of the disintegration cell and become immobilized.

Portions of the above-described embodiments of the present invention can be implemented using one or more computer systems, for example to perform image processing and analysis. For example, the embodiments may be implemented using hardware, software or a combination thereof. When implemented in software, the software code can be stored on any form of non-transient computer-readable medium and loaded and executed on any suitable processor or collection of processors, whether provided in a single computer or distributed among multiple computers.

Experimental

Six different types of commercial RDTs and one type of laboratory manufactured placebo RDT were used to test and validate the viability of the fabricated disintegration apparatus. RDTs used in the study are listed in Table 1.

TABLE 1

RDTs used in the study

| Product | Type | Manufacturer |
| --- | --- | --- |
| Nimulid ® - MD | Commercial product | Panacea Biotec Ltd. |
| Nicip MD | Commercial product | Cipla Ltd. |
| Tolaz - MD 5 | Commercial product | Torrent Pharmaceuticals Ltd. |
| Vomikind ® - MD 4 | Commercial product | Pharma Force Lab. |
| Vomistop 10 DT | Commercial product | Cipla Ltd. |
| Glyprin ™ | Commercial product | UPHA Pharmaceutical Mfg. |
| Placebo RDT | Prepared in laboratory | Not applicable |

Mannitol (89.5%), crospovidone (10%) and magnesium stearate (0.5%) were used to prepare the placebo RDT by direct compression method. Both mannitol and crospovidone were dry blended for 10 min, magnesium stearate was then added to these tablet constituents and the mixture was further blended for an additional 2 minutes. The mixture was later compressed using a single punch tablet press, equipped with flat faced punches. All types of RDTs were randomly inscribed from a to g and thus the identity of RDT was concealed during the experiment. Six samples of each type of RDTs were used for each experiment. Water was used as a disintegration medium. The RDT was first placed into the designated cylindrical place of a disintegration chamber. Next, the disintegration medium was introduced into the disintegration chamber using a peristaltic pump. Five different flow rates (48 mL/min, 74 mL/min, 97 mL/min, 120 mL/min and 146 mL/min) were tested to identify the optimum flow rate of the disintegration medium. No complete disintegration of RDT was observed with the flow rate of 48 mL/min. Flow was not sufficient to disintegrate the tablet mass and remove the disintegrated tablet fragments from the disintegration chamber. Complete disintegration and removal of tablet parts were observed when flow rates of 74 mL/min and 97 mL/min flow were used. At the flow rates of 120 mL/min and 146 mL/min, swirling of tablet core was observed for some time point before complete disintegration.

Figure 6:
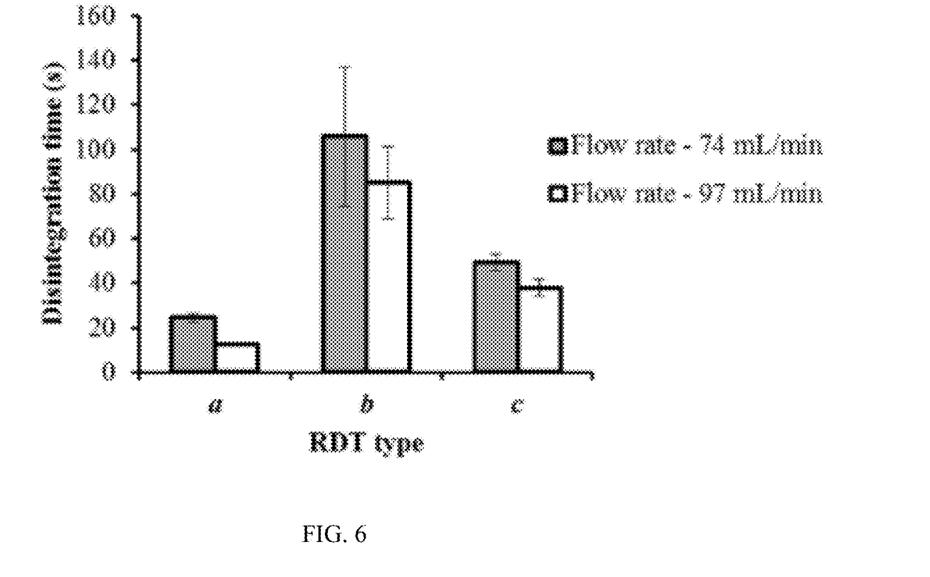
FIG. 6 is a graph of disintegration time of Rapidly Disintegrating Tablets (RDTs) measured using a disintegration apparatus in accordance with a version of the invention at different flow rates.

FIG. 6 is a graph of the disintegration time of the RDTs measured using the disintegration apparatus in accordance with a version of the invention at different flow rates. Disintegration measurements of three different RDTs (inscribed as a, b and c) were performed using the fabricated disintegration apparatus at the flow rate of 74 mL/min and 97 mL/min. Relative standard deviation (R.S.D.) of disintegration time was calculated as a measurement of precision. Smaller R.S.D (in the range of 6.1%-18.4%) was observed with the flow rate of 97 mL/min in comparison with 74 mL/min (in the range of 7.5-29.6%). Therefore, 97 mL/min was chosen further as an optimized flow rate for disintegration study using the fabricated disintegration apparatus.

Figure 7:
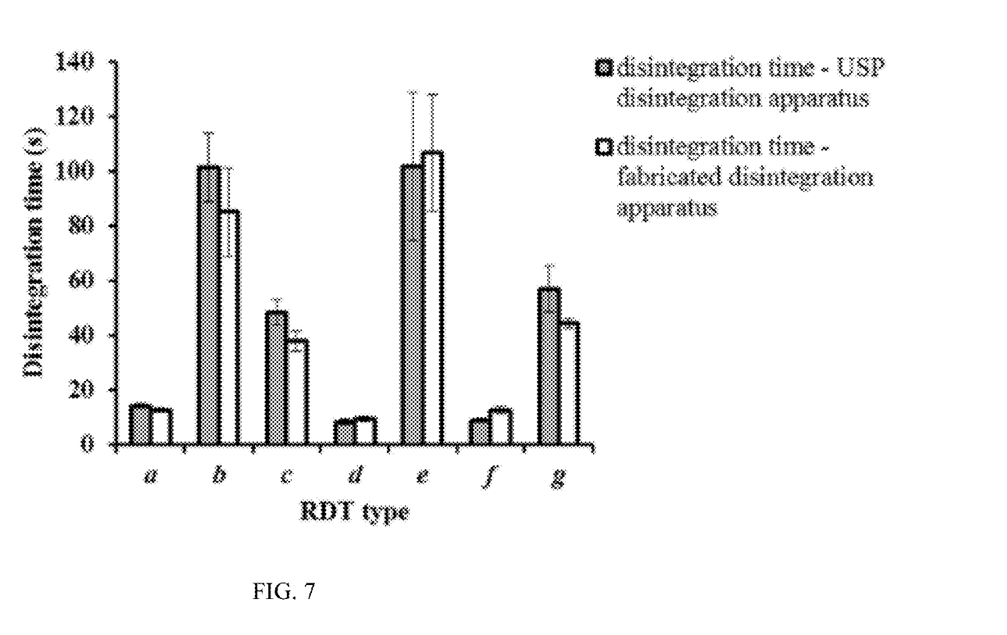
FIG. 7 is a graph of disintegration time of Rapidly Disintegrating Tablets (RDTs) measured using both a United States Pharmacopoeia (USP) disintegration apparatus and a disintegration apparatus according to a version of the invention.

Disintegration times of seven different types of RDTs (inscribed as a to g) were measured using the fabricated disintegration apparatus and method mentioned in the summary of invention with the flow rate of 97 mL/min. Sometimes, a transparent layer was fixed 5 mm or thereabouts above of the disintegration cell so that the occasional bubble formation could be prevented and clearer images can be captured. For a better comparison, disintegration times of RDTs were also evaluated using the conventional USP disintegration apparatus. Briefly, the RDT was introduced into the tube of USP disintegration apparatus when it is at its highest point. The timer was started upon introduction of RDT and disintegration time was noted down once the disintegrated tablet completely passes through the sieve of the apparatus tube. FIG. 7 is a graph of the disintegration time of the RDTs measured using both the USP disintegration apparatus and the disintegration apparatus according to a version of the invention.

Figure 8:
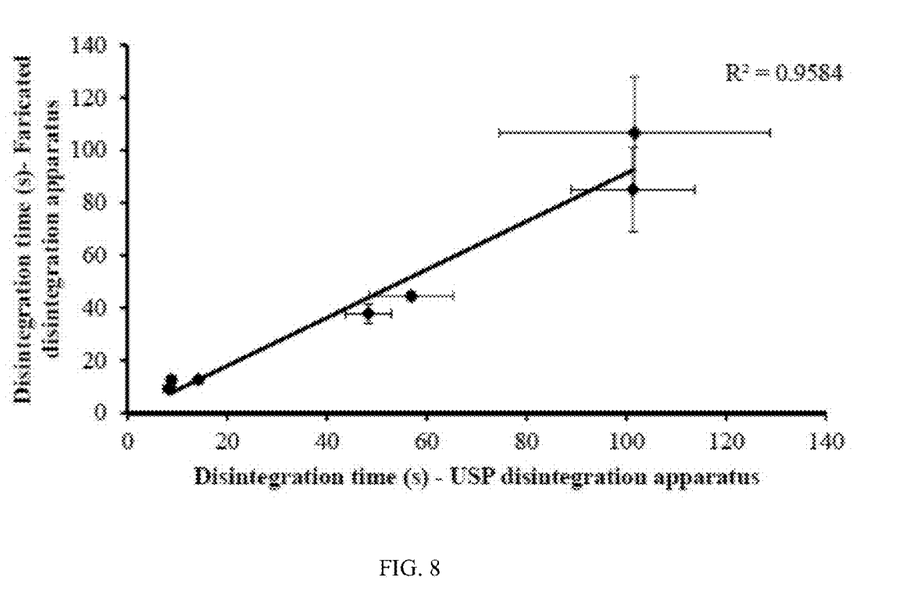
FIG. 8 is a graph of the relationship in disintegration time obtained by the disintegration apparatus according to a version of the invention and the United States Pharmacopoeia (USP) disintegration apparatus.

FIG. 8 is a graph of the relationship in disintegration time obtained by the disintegration apparatus according to a version of the invention and the USP disintegration apparatus. A strong correlation ($R^2$=0.9584) was obtained between the disintegration times obtained using both the apparatus. Smaller R.S.D. (in the range of 3.6-19.9%) was observed for the results obtained using the fabricated disintegration apparatus in comparison to the USP disintegration apparatus (in the range of 5.6-26.7%), suggesting a better precision in measurement. As it is sometimes difficult to determine the disintegration time of RDT using USP disintegration apparatus due to the rapidness of disintegration process, the fabricated disintegration apparatus is an adequate and accurate suitable option for RDT disintegration study.

While this invention has been particularly shown and described with references to example embodiments thereof, it will be understood by those skilled in the art that various changes in form and details may be made therein without departing from the scope of the invention encompassed by the appended claims.

What is claimed is:

1. An apparatus for determining the disintegration time of a disintegrating dosage form, the apparatus comprising:
    a disintegration cell configured to contain the dosage form; and
    a first liquid jet inlet and a second liquid jet inlet, the first liquid jet inlet and the second liquid jet inlet being positioned on opposite sides of the disintegration cell and unaligned with each other, the first liquid jet inlet and the second liquid jet inlet being configured to introduce a disintegration medium into the disintegration cell simultaneously through the first liquid jet inlet and the second liquid jet inlet to produce a swirling shear force of the disintegration medium within the disintegration cell;
    the disintegration cell comprising an overhead outlet configured to remove, from the disintegration cell, overflowing disintegration medium and a plurality of disintegrated fragments of the dosage form.

2. An apparatus according to claim 1, wherein the disintegration cell is configured to permit visualization of the dosage form through at least a portion of the disintegration cell.

3. An apparatus according to claim 2, wherein the disintegration cell comprises a transparent surface configured to allow passage of light from a light source to permit visualization of the dosage form.

4. An apparatus according to claim 2, wherein the disintegration cell comprises a reflecting surface configured to reflect light, received from a light source, to permit visualization of the dosage form.

5. An apparatus according to claim 2, further comprising a camera mounted to permit the visualization of the dosage form.

6. An apparatus according to claim 5, further comprising a collimating lens mounted to pass light, received from the disintegration cell, to the camera.

7. An apparatus according to claim 5, further comprising a data acquisition system configured to receive from the camera an electronic signal indicative of an image of at least a portion of the disintegration cell.

8. An apparatus according to claim 2, further comprising an image projection system mounted to permit visualization of the dosage form.

9. An apparatus according to claim 1, further comprising a liquid pump in fluid communication with the disintegration cell.

10. An apparatus according to claim 1, wherein the disintegration cell is cylindrical.

11. An apparatus according to claim 1, wherein the dosage form comprises a tablet.

12. An apparatus according to claim 1, further comprising a retaining mesh configured to permit passage of the overflowing disintegration medium and the plurality of disintegrated fragments of the dosage form to be removed from the disintegration cell, and to retain fragments of the dosage form that are larger than a mesh aperture size of the retaining mesh.

13. An apparatus according to claim 1, wherein each of the first liquid jet inlet and the second liquid jet inlet comprises a lower inlet base at a same level as a base of the disintegration cell.

14. An apparatus according to claim 13, wherein at least one of the first liquid jet inlet and the second liquid jet inlet comprises an inlet from the group consisting of: an L-shaped inlet; an inlet comprising a C-shape; and a triangle-shaped inlet.

15. An apparatus according to claim 1, wherein the first liquid jet inlet and the second liquid jet inlet are configured to produce the swirling shear force at a substantially consistent level of shear force that disintegrates the dosage form in a time substantially equivalent to a disintegration time produced by gentle mastication of the dosage form, and to enable breakdown of the dosage form.

16. An apparatus according to claim 1, the first liquid jet inlet and the second liquid jet inlet delivering the disintegration medium into the disintegration cell at a flow rate of between about 65 milliliters per minute and about 105 milliliters per minute.

17. A method for determining the disintegration time of a disintegrating dosage form, the method comprising:
    simultaneously introducing a disintegration medium into a disintegration cell through a first liquid jet inlet and a second liquid jet inlet, the first liquid jet inlet and the second liquid jet inlet being positioned on opposite sides of the disintegration cell and unaligned with each other, the disintegration cell containing the dosage form, the introducing producing a swirling shear force of the disintegration medium within the disintegration cell;
    removing overflowing disintegration medium and a plurality of disintegrated fragments of the dosage form from the disintegration cell through an overhead outlet; and
    imaging a disintegration process of the dosage form through at least a portion of the disintegration cell to permit determining a disintegration end point time of the dosage form.

18. A method according to claim 17, comprising using a video camera to image the disintegration process.

19. A method according to claim 17, comprising using an image projection system to image the disintegration process.

20. A method according to claim 17, further comprising:
    using a data acquisition system to receive an electronic signal indicative of an image of at least a portion of the disintegration cell; and
    performing image analysis of the electronic signal to determine the disintegration end point time of the dosage form.

21. A method according to claim 17, wherein the simultaneously introducing the disintegration medium into the disintegration cell through the first liquid jet inlet and the second liquid jet inlet comprises delivering the disintegration medium into the disintegration cell at a flow rate of between about 65 milliliters per minute and about 105 milliliters per minute.

* * * * *